United States Patent
Cover et al.

(10) Patent No.: US 7,872,446 B2
(45) Date of Patent: Jan. 18, 2011

(54) SUBMERSIBLE/STERILIZABLE BATTERY

(75) Inventors: Reid Cover, Mountain View, CA (US); Emmet McCarthy, Gilroy, CA (US)

(73) Assignee: Stryker Corporation, Kalamazoo, MN (US)

( * ) Notice: Subject to any disclaimer, the term of this patent is extended or adjusted under 35 U.S.C. 154(b) by 478 days.

(21) Appl. No.: 12/152,082

(22) Filed: May 12, 2008

(65) Prior Publication Data
US 2008/0284372 A1 Nov. 20, 2008

Related U.S. Application Data

(60) Provisional application No. 60/930,083, filed on May 14, 2007.

(51) Int. Cl.
*H02J 7/00* (2006.01)
*F21L 4/00* (2006.01)
*A61B 1/00* (2006.01)
*H01M 2/10* (2006.01)

(52) U.S. Cl. ................ 320/112; 320/107; 320/110; 320/114; 362/183; 362/190; 362/572; 600/101; 600/133; 429/97; 429/99; 429/175; 307/150

(58) Field of Classification Search .............. 320/112
See application file for complete search history.

(56) References Cited

U.S. PATENT DOCUMENTS

| | | | |
|---|---|---|---|
| 3,643,083 A * | 2/1972 | Heine | 320/135 |
| 4,109,062 A | 8/1978 | McCartney et al. | |
| 4,146,682 A | 3/1979 | Nakao | |
| 5,149,598 A | 9/1992 | Sunshine | |
| 5,178,131 A | 1/1993 | Upsher | |
| 5,476,729 A | 12/1995 | Miller, Jr. et al. | |
| 5,782,654 A | 7/1998 | Inazuka et al. | |
| 5,865,727 A * | 2/1999 | Sano et al. | 600/178 |
| 6,260,994 B1 | 7/2001 | Matsumoto et al. | |
| 6,318,887 B1 | 11/2001 | Matsumoto | |
| 6,461,764 B1 | 10/2002 | Nakamura | |
| 6,641,432 B1 | 11/2003 | Ouyoung | |
| 6,659,943 B2 * | 12/2003 | Watanabe et al. | 600/178 |
| 6,737,579 B1 | 5/2004 | Laufer et al. | |
| 6,847,190 B2 | 1/2005 | Schaefer et al. | |
| 6,866,962 B2 | 3/2005 | Bechtold et al. | |
| 6,917,183 B2 | 7/2005 | Barlev et al. | |

(Continued)

*Primary Examiner*—Edward Tso
*Assistant Examiner*—Yalkew Fantu
(74) *Attorney, Agent, or Firm*—Flynn, Thiel, Boutell & Tanis, P.C.

(57) ABSTRACT

A battery pack for a sterilizable instrument, such as a medical endoscope. The battery pack includes batteries removably positioned within an enclosure which mounts a first grouping of electrical contacts engaged with the battery contacts. The enclosure includes an outer end wall which sealingly encloses the first grouping of contacts. The outer end wall mounts a second grouping of electrical contacts which are normally resiliently maintained in a first position spaced from the contacts of the first grouping. The contacts of the second grouping sealingly penetrate through the outer end wall. When the battery pack is engaged on the instrument, the contacts of the second grouping engage third contacts on the instrument, causing the contacts of the second grouping to move into a second position where they directly engage contacts of the first grouping to provide electrical power to the instrument. When the battery pack is removed from the instrument, the contacts of the second grouping are resiliently returned to the first position, whereupon the batteries can be sterilized.

11 Claims, 7 Drawing Sheets

U.S. PATENT DOCUMENTS

| | | | |
|---|---|---|---|
| 7,198,625 B1 * | 4/2007 | Hui et al. ..................... 606/41 |
| 2002/0098410 A1 | 7/2002 | Leysieffer et al. |
| 2003/0193314 A1 * | 10/2003 | Solingen .................... 320/107 |
| 2004/0143297 A1 * | 7/2004 | Ramsey, III ................... 607/5 |
| 2006/0040171 A1 * | 2/2006 | Lee ............................. 429/61 |
| 2006/0085969 A1 | 4/2006 | Bennett et al. |
| 2006/0220613 A1 | 10/2006 | Abe |

* cited by examiner

SUBMERSIBLE/STERILIZABLE BATTERY

CROSS REFERENCE TO RELATED APPLICATION

This application claims the benefit of U.S. Provisional Application Ser. No. 60/930,083, filed May 14, 2007, which is incorporated herein by reference in its entirety.

FIELD OF THE INVENTION

This invention relates to a portable hand-held battery-powered tool or instrument, particularly a medical instrument such as an endoscope, and more specifically relates to an improved submersible or sterilizable battery pack for such instrument.

BACKGROUND OF THE INVENTION

The use of rechargeable batteries within powered medical instruments, for example surgical devices such as endoscopes and the like, is well known. The powering of such devices by batteries is desirable due to the highly improved mobility and flexibility of use provided by the instrument being free of connection to power cords. The use of rechargeable batteries for powering such devices, however, presents additional complications, particularly with respect to the need to sterilize such instruments prior to use.

In some instruments the batteries are cleaned utilizing various solutions, but are not fully sterilized by insertion into an autoclave, and the cleaned batteries are carefully inserted into an interior chamber of the sterilized instrument. This process, however, involves risk of contamination of the sterilized instrument during insertion of the batteries since the latter are not fully sterilized.

To overcome the risk associated with instruments of the aforementioned type, in some situations the batteries themselves are sterilized, such as by positioning them in an autoclave similar to the sterilization technique utilized on the instrument. Autoclaving of the batteries, however, can be damaging to the batteries themselves by decreasing the life and recharging capacity of the batteries. Further, positioning of the batteries in an autoclave exposes the battery contacts to the sterilizing fluid, and can result in shorting out and hence destruction of the battery.

To minimize this latter risk, various battery packs and related equipment have been developed which sequentially discharge, then sterilize, and then recharge the batteries prior to the battery pack being reinserted into the sterilized instrument. Such arrangements, however, not only significantly complicate the overall equipment required, but also complicate the processing steps, whereby the overall sterilizing process of the instrument and of the battery pack is more complex than desired.

Accordingly, it is an object of this invention to provide an improved battery pack for a medical device, such as a surgical instrument, which battery pack can be easily and safely handled without exposing the contacts of the battery to the sterilizing fluid so as to minimize the risk of short circuiting the battery, thereby overcoming many of the disadvantages and complexities associated with prior known battery packs and sterilizing techniques as associated with such medical instruments.

In accordance with the present invention, there is provided an improved battery pack for a sterilizable instrument, such as a medical endoscope. The battery pack typically includes two or more rechargeable batteries which are removably positioned within a chamber defined interiorly of a housing or enclosure. The enclosure includes an inner end wall which mounts a first grouping of electrical contacts which are engaged with the battery contacts when the batteries are disposed within the enclosure chamber. The enclosure includes an outer end wall which is sealingly engaged to the enclosure and which sealingly encloses the inner end wall and the first grouping of contacts mounted thereon. The outer end wall mounts a second grouping of electrical contacts which are normally resiliently maintained in a first position wherein they are spaced outwardly from and hence maintained in non-engaged relationship relative to the contacts of the first grouping. The contacts of the second grouping are sealingly engaged with but penetrate through the outer end wall so that, when the battery pack is properly positionally engaged on the instrument, the contacts of the second grouping engage a third grouping of contacts as fixed on the instrument, which causes the contacts of the second grouping to be moved or deflected into a second position whereby they directly engage contacts of the first grouping, thereby causing the contacts of the second grouping to conductively bridge directly between the contacts of the first and third groupings so as to provide electrical power to the instrument. When the battery pack is removed from the instrument, the contacts of the second grouping are automatically resiliently returned to the first position wherein they are spaced from the contacts of the first grouping, whereupon the batteries can be sterilized while at the same time the outer wall sealingly encloses the contacts of the first grouping and prevents them from being contacted by the sterilizing fluid, thereby minimizing the risk of short circuiting. While the contacts of the second grouping are exposed to the sterilizing fluid, these contacts are not electrically coupled to the battery when the contacts are resiliently urged into the second position, and hence present no risk with respect to battery damage.

In a first embodiment of the invention, the outer end wall of the battery pack enclosure carries thereon a resiliently flexible diaphragm or membrane, the latter in turn having the contacts of the second grouping carried thereon. The membrane is normally resiliently urged into a position wherein it abuts the outer end wall so as to maintain the second contacts spaced from the first contacts, with the second contacts being moved against the resilient urging of the diaphragm into engagement with the first contacts only when the battery pack is fully engaged in the instrument so as to cause the second contacts to engage the third contacts as fixed to the instrument.

In a second embodiment of the battery pack according to the invention, the contacts defining the second grouping are mounted directly on the outer end wall, being sealingly but slidably supported thereon so as to penetrate the end wall while being movable relative thereto between the first and second positions. The individual contacts of the second grouping are urged outwardly by small springs or equivalent resilient structures into the first position wherein they project outwardly away from the outer end wall to prevent their being in contacting engagement with the first contacts when the battery pack is disengaged from the instrument, thereby permitting safe sterilizing of the battery pack. In this latter condition, the pressure applied by the sterilizing fluid acts only against a very small area as defined by the contacts, and hence is incapable of affecting inward displacement of the second contacts toward the first contacts in opposition to the urging of the contact springs.

Other objects and purposes of the present invention will be apparent to persons familiar with arrangements of the general type described herein upon further reading of the invention as described and illustrated herein.

Certain terminology will be used in the following description for convenience in reference only, and will not be limiting. For example, the words "upwardly", "downwardly", "rightwardly" and "leftwardly" will refer to directions in the drawings to which reference is made. The words "inwardly" and "outwardly" will refer to directions toward and away from, respectively, the geometric center of the instrument or battery pack, and designates parts thereof. Said terminology will include the words specifically mentioned, derivatives thereof, and words of similar import.

DETAILED DESCRIPTION

Figure 1:
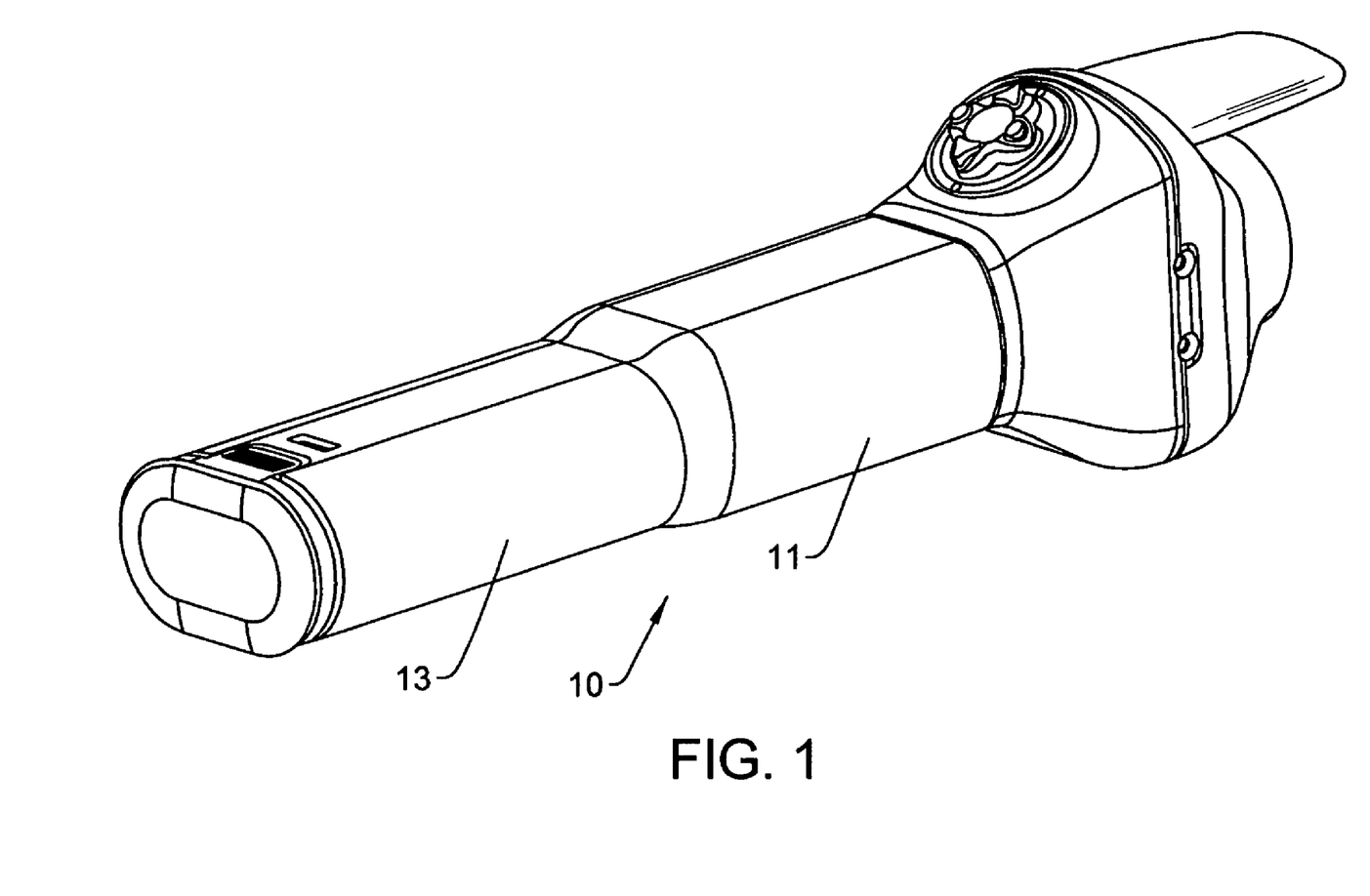
FIG. 1 is a perspective view of an instrument, specifically a medical endoscope, employing a battery pack according to the present invention, the instrument being illustrated with the tip portion removed for clarity of illustration.
Figure 2:
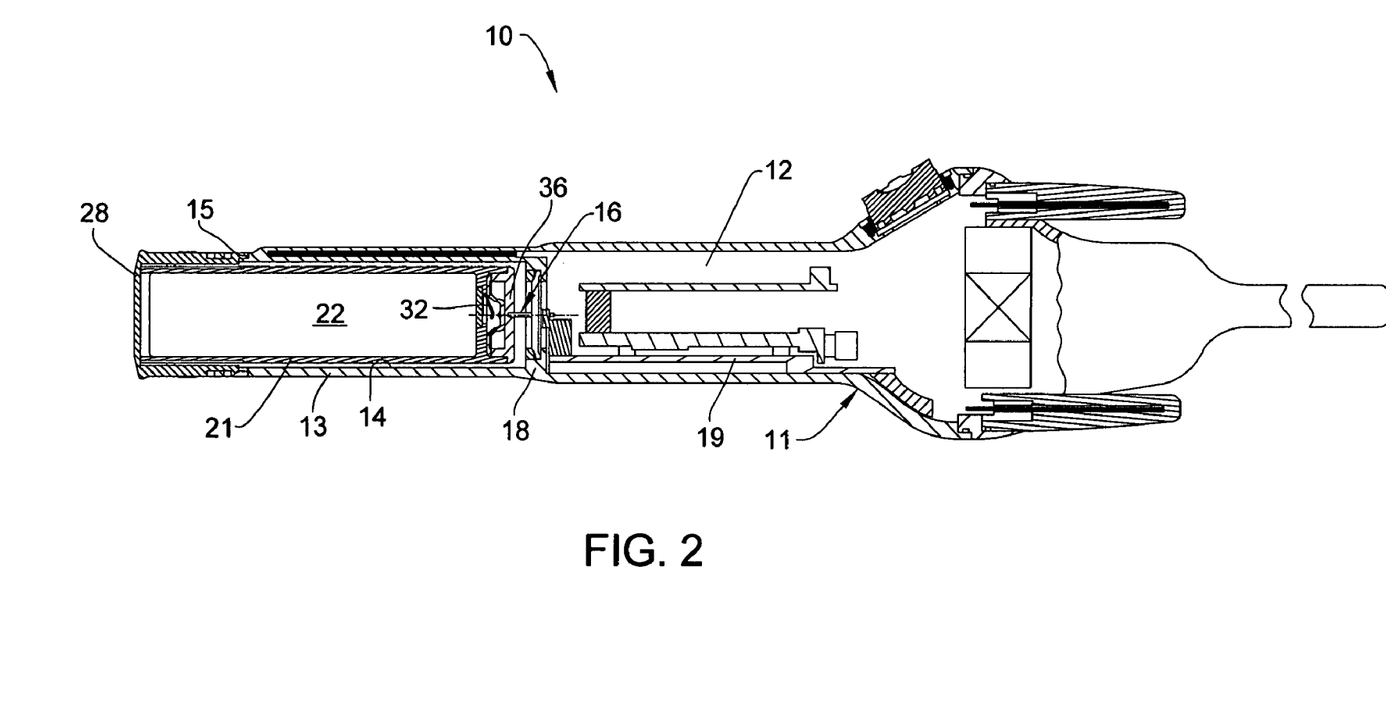
FIG. 2 is a partial cross-sectional view of the endoscope of FIG. 1 and illustrating the mounting thereon of a battery pack according to the present invention mounted thereon.

Referring to FIGS. 1 and 2, there is diagrammatically illustrated a portable battery-powered instrument or device 10, such as an endoscope, utilized for performing various medical procedures. The overall construction of the endoscope 10, and the specifics of the tools used in association therewith, is dependent upon the exact type of medical procedure being carried out, which variations are well known so that further detailed description of the details and features of the endoscope are believed unnecessary.

The battery powered device 10 includes a housing 11 which is configured so as to be conveniently manually gripped and hence function as a handpiece, with the housing defining therein an interior chamber 12 for accommodating the necessary components associated with the device. The housing 11 in the illustrated embodiment includes a sleeve-like wall 13 for defining therein an interior chamber 14 to accommodate a removable batter pack (described hereinafter). The chamber 14 is accessible through an opening 15 associated with one end of the sleeve structure, which opening is closed off when the battery pack is positioned within the chamber 14.

The housing 11 includes an inner or rear wall 18 which effectively projects across and closes off the inner end of the battery pack chamber 14. This wall 18 mounts thereon a first grouping 16 of contacts, which in the illustrated embodiment includes a plurality of individual first electrical contacts 17 (FIG. 7) which are generally positioned in sidewardly spaced relationship and protrude outwardly from the rear wall 18. The contacts 17 associated with the first grouping 16 protrude inwardly into the interior of the housing 11 for connection to suitable conductors which in turn join to appropriate electrical control structure provided within the housing, such as a control board or panel 19 which, in a conventional manner, is provided with appropriate programming to provide desired electrical control of the endoscope functions. The construction of the interior electrical structure of the instrument, such as the control panel and its associated connections and functions, is conventional and/or modified in accordance with the desired instrument functions, whereby further detailed description thereof is believed unnecessary.

The contacts 17 which make up the grouping 16 and which protrude outwardly from the end wall 18 protrude into the battery pack chamber 14 so as to make electrical contact with the battery pack when the latter is installed into the chamber 14 to hence permit powering of the instruments with a low-voltage direct-current. These contacts 17 hence function as electrical input contacts for the instrument.

In accordance with the present invention, the instrument 10 is provided with an improved battery pack 21 which is releasably and removably accommodated within the chamber 14 of the housing 11 to provide direct-current energization of the instrument contacts 17. The battery pack 21, as illustrated by FIGS. 3-6, typically includes two or more rechargeable batteries 22 which are sealingly enclosed within a surrounding housing or enclosure 23, the latter defining therein an interior battery chamber 24 which is sized and shaped to accommodate the desired number, here two, of batteries 22.

The battery pack enclosure 23 includes a main body 25 having an outer tubular side wall 26 which at one end is closed off by a transversely extending inner end wall 27. The outer end of the main body 25 is open, and sealingly mounts thereon a removable end cap or cover 28 for sealingly closing off the interior battery chamber 24. The end cover 28 has a pair of latching tabs 29 protruding transversely inwardly from adjacent opposite sides thereof in generally parallel relationship. The protruding tabs 29 are slidably guided within recesses 30 formed in the opposite sides of the tubular side wall 26 when the end cover is mounted on the main body 25. The latching tabs 29, specifically the latching parts provided at the outer free ends thereof, resiliently snap into latching engagement within recesses or openings associated with the end of the sleeve-like housing wall 13 to latchingly engage the battery pack 21 within the chamber 14 of the housing 11 substantially as illustrated in FIG. 2.

The inner end wall 27 of the battery pack enclosure mounts thereon a grouping 31 of contacts which includes a plurality of separate second contacts 32 which are disposed in sidewardly adjacent but spaced relationship with one another. These contacts 32 are mounted on a contact support member 33 which is stationarily carried on the end wall 27 and which creates electrical contacting engagement with the electrical contacts defined on the adjacent ends of the batteries 22. The contacts 32 hence are supplied with amperage from the batteries, and constitute the "live" contacts of the battery pack.

Figure 5:
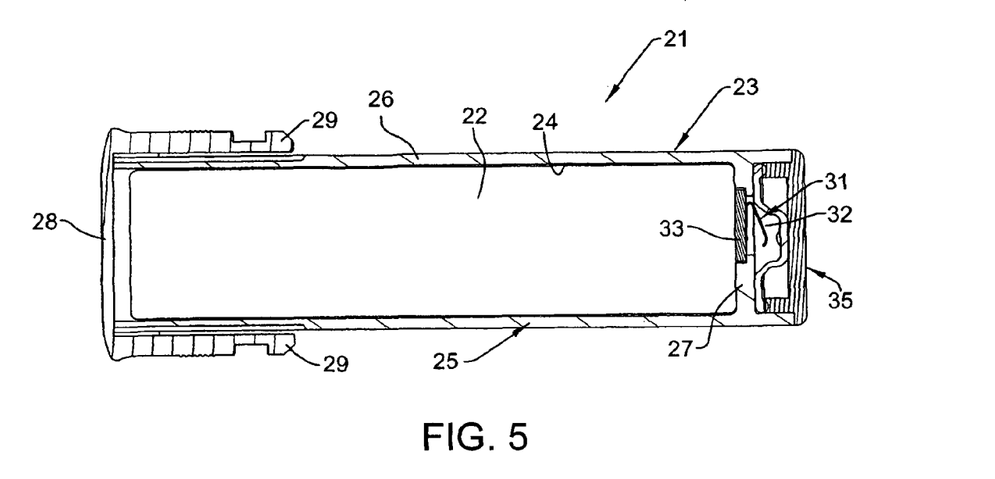
FIG. 5 is a sectional view taken generally along lines 5-5 in FIG. 4.
Figure 6:
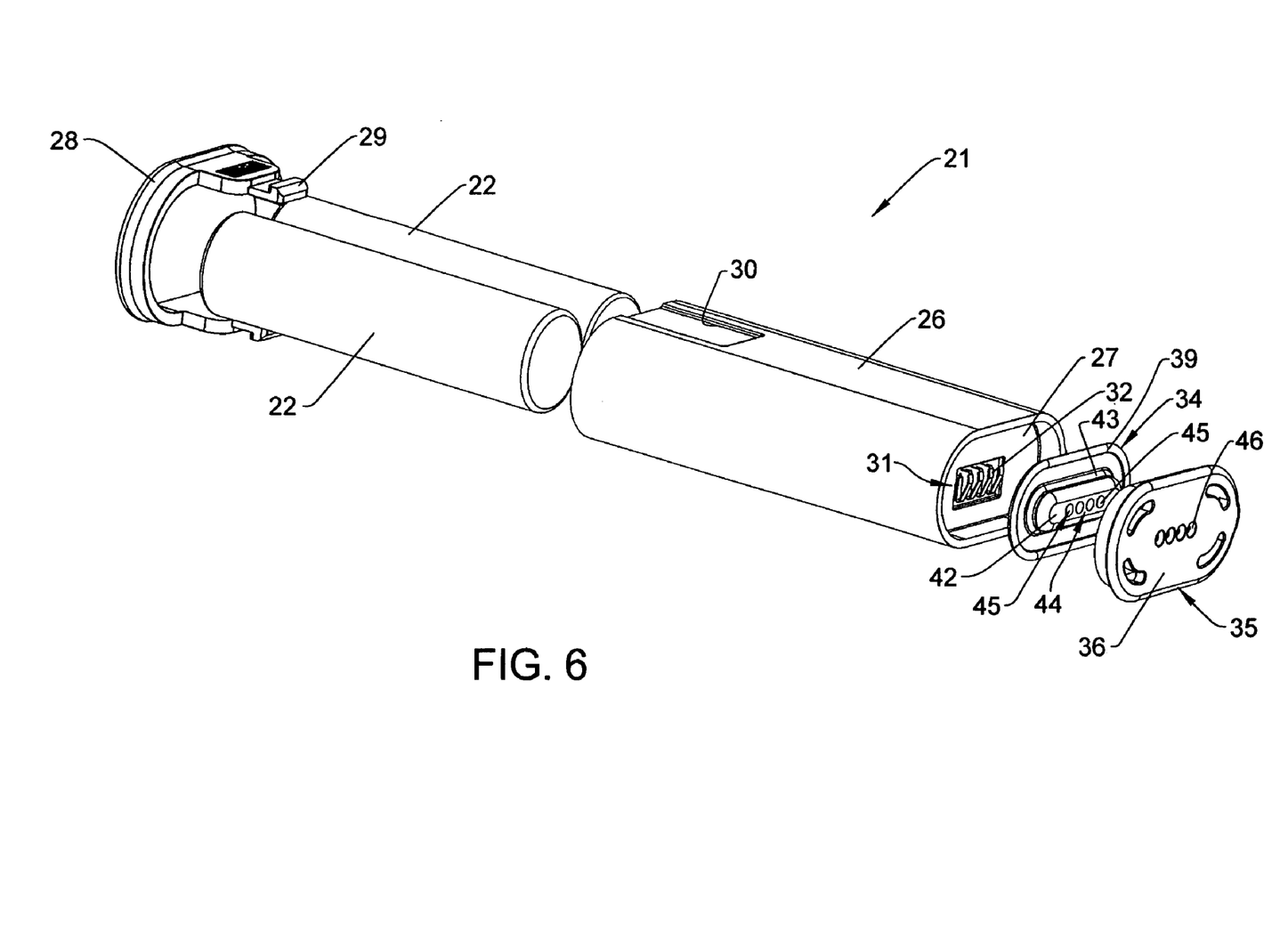
FIG. 6 is a perspective view of the battery pack shown in an exploded or separated condition.

The "live" contacts 32 preferably protrude outwardly away from the support member 33 in a direction toward the adjacent end of the battery pack. The contacts 32 are preferably constructed in a manner so as to possess at least limited inward resilient deflectability when engaged with another contact (as described hereinafter) to ensure intimate contacting engagement sufficient for proper transmission of direct electrical current therethrough. The contacts 32 may, as illustrated in FIG. 5, be constructed similar to a resiliently deflectable cantilevered spring.

Figure 3:
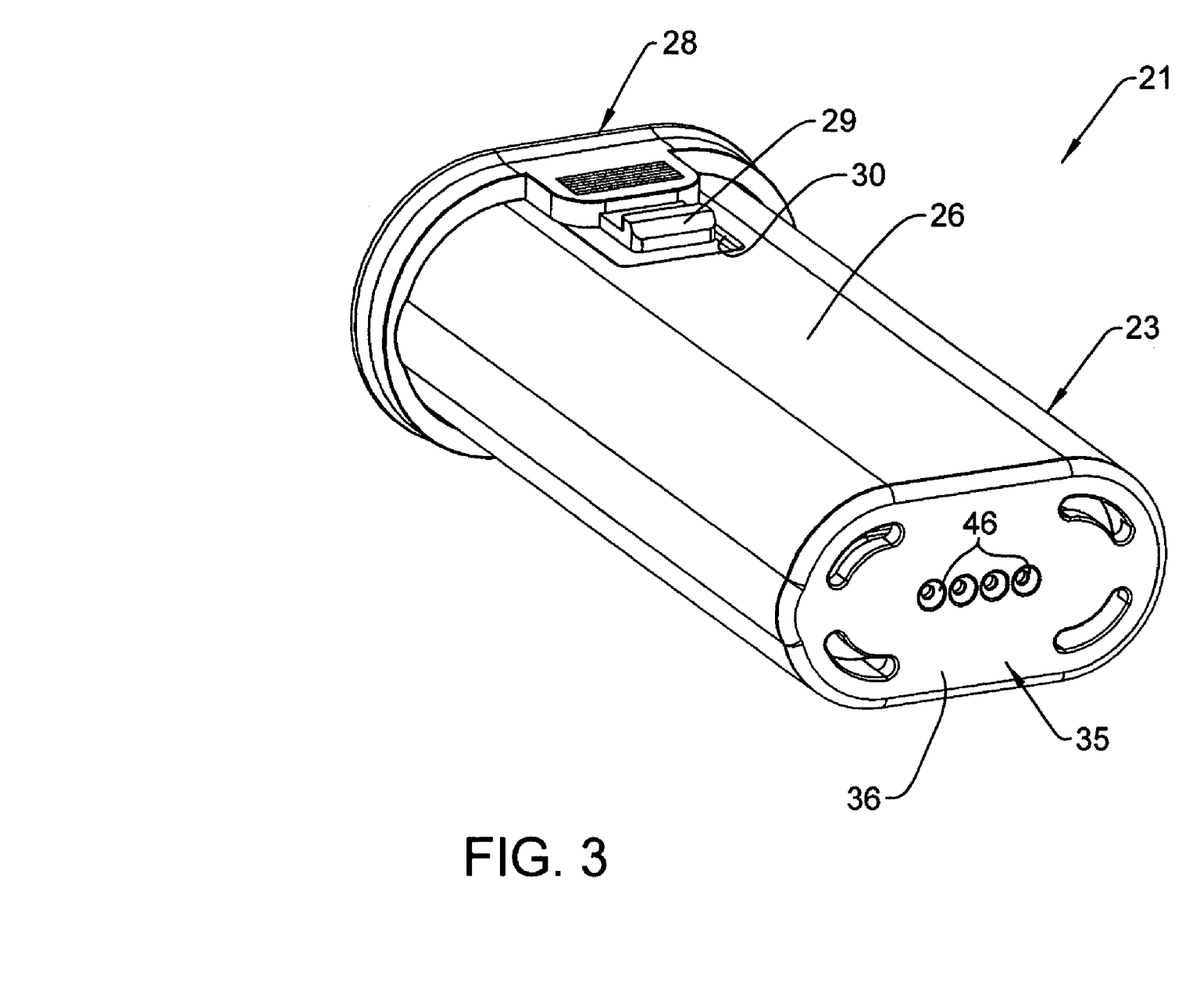
FIG. 3 is a perspective view of the battery pack according to the present invention, the battery pack being shown removed from the endoscope.
Figure 4:
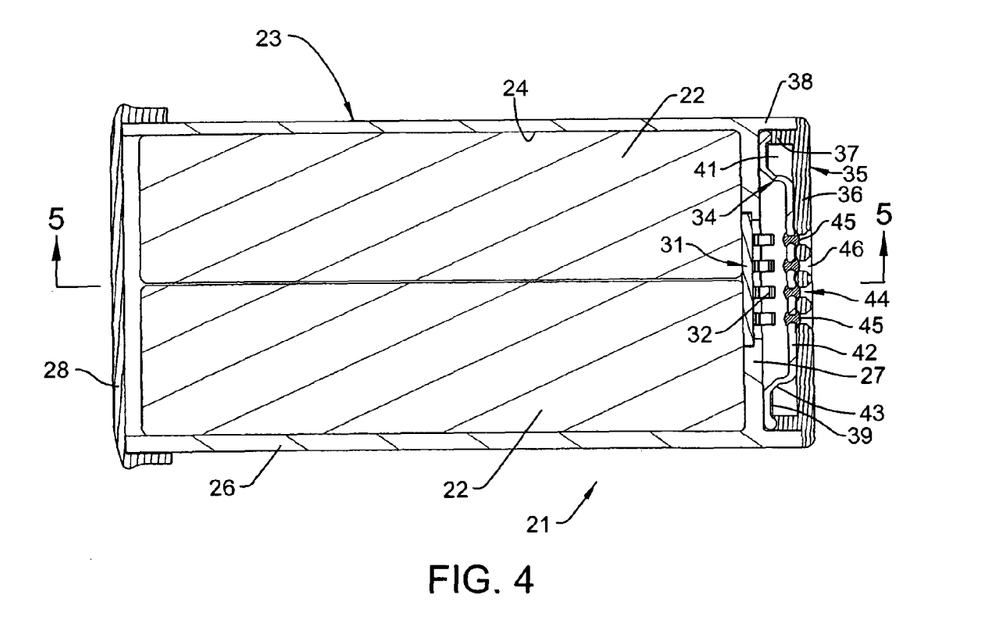
FIG. 4 is a central planar sectional view of the battery pack shown in FIG. 3.

The battery pack 21, as illustrated in FIGS. 3-6, also includes an outer end cap 35 which extends transversely across and closes off the inner end of the sleeve-like side wall 26 of the battery enclosure 23. This end cap 35 includes a basic end wall 36 which extends transversely across the end of the sleeve-like side wall 26, and the end wall 36 has an edge flange 37 which protrudes inwardly from the end wall 36 and which is positioned so that the flange 37 is snugly engaged with the inner wall of the sleeve-like side wall 26. As illustrated by FIG. 4, the inner end wall 27 is spaced slightly inwardly from the free end of the sleeve-like side wall 26, thereby defining a sleeve-like flange part 38 which protrudes outwardly beyond the inner end wall 27. The end cap 35 extends transversely across and sealingly cooperates with this sleeve-like flange part 38 so as to close off the end of the enclosure 23 opposite the end which accommodates the removable end cap 28.

The disposition of the end cap 35 relative to the inner end wall 27 is such that the outer end wall 36 and inner end wall 27 are spaced apart longitudinally of the enclosure, thereby defining a chamber or space 41 therebetween.

The end wall 36, in cooperation with the sleeve-like side wall 26, mounts thereon a further grouping 44 of electrical contacts, the latter including a plurality of individual third electrical contacts 45 which are sidewardly spaced apart and which function to create an electrical contacting bridge between the live battery contacts 32 and the instrument contacts 17 when the battery pack 21 is engaged or seated with the endoscope.

The contact grouping 44 is provided on a support member 34 which, in the illustrated embodiment, comprises a resiliently-deflectable membrane which is positioned within the chamber 41 and extends substantially transversely thereacross, with the edge part 39 of the membrane 34 being clampingly seated against the inner end wall 27 by the end cap flanges 37. The membrane 34 has a center part 42 which joins to the annular edge part 39 through an intermediate annular part 43, the latter being sufficiently pre-formed to have a generally truncated conical shape so as to resiliently urge the center part 42 outwardly away from the plane of the edge flange 37, with the overall sizing and positioning being such that the center part 42 is normally urged into contacting engagement with the inner surface of the outer end wall 36 substantially as illustrated in FIGS. 4 and 5.

The contacts 45 are carried on the center part 42 of the flexible membrane, with the individual contacts 45 each being sealingly seated on and protruding through the thickness of the center part 42 of the membrane 34 whereby the contact 45 has exposed contacting surfaces on opposite ends thereof, which surfaces are hence accessible from opposite sides of the membrane.

In the illustrated arrangement, the enclosure end wall 36 has a plurality of small sidewardly-spaced openings 46 extending therethrough, which openings generally correspond to and longitudinally align with the individual contacts 45. The openings 46 also align with the instrument contacts 17 when the battery pack is mounted thereon. The bridging contacts 45 are disposed in longitudinal alignment with the respective battery live contacts 32, but are normally spaced and hence disengaged therefrom whenever the battery pack is disengaged from the instrument contacts 17.

While use of the battery pack 21 according with the present invention is believed apparent from the aforementioned description, nevertheless its use will now be briefly described to ensure a complete understanding thereof.

With the battery pack 21 in its assembled condition substantially as illustrated by FIGS. 3-5, the battery pack containing the batteries 22 within the enclosure 23 can be sterilized since the batteries 21 and the live contacts 32 are effectively isolated from the sterilizing fluid, such as any fluid which contacts the battery pack during sterilizing thereof, such as sterilizing within an autoclave. In this respect, the resiliency of the membrane 34 always urges the bridging contacts 45 outwardly away from the live contacts 32 so that, even though sterilizing fluid may contact the bridging contacts 45 and may also gain access to the subchamber 41 defined between the membrane 34 and the outer end wall 36, nevertheless the membrane 34 prevents the sterilizing fluid from accessing the subchamber located behind the membrane 34 so that the live battery contacts 32 are not exposed to the sterilizing fluid, and thus the possibility of short circuiting across the live contacts 32 is greatly minimized.

Of course, when replacement of the batteries 22 is desired, the end cap 28 is removed, the old batteries removed from the enclosure and replaced with new batteries, following which the end cap is again sealingly mounted on the enclosure and the entire battery pack sterilized so as to place it in a condition for use.

Figure 7:
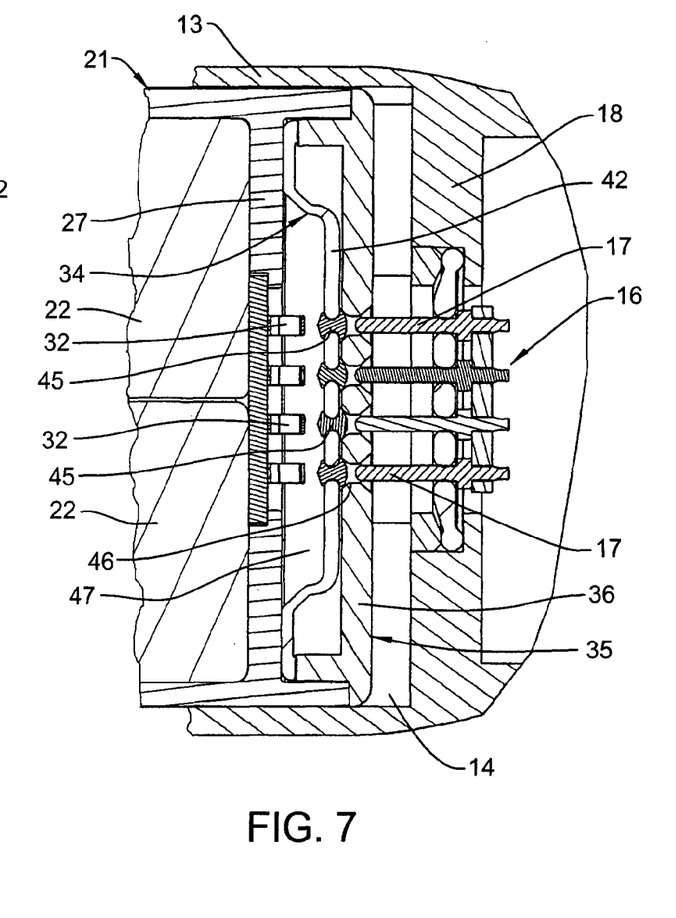
FIG. 7 is an enlarged fragmentary sectional view which illustrates the contact arrangement associated with the end of the battery pack, and the opposed contacts provided on the instrument, the contacts being shown in a disengaged position just prior to the battery pack being fully seated and engaged with the instrument.

When use of the sterilized battery pack 21 is desired, the battery pack is slidably inserted into the open end of the housing sleeve 13 associated with the instrument handpiece 11, the latter having already been sterilized. During the insertion of the battery pack into the handpiece, the battery pack is slidably inserted inwardly until it reaches a position close to but not yet fully seated, whereupon the various contacts are still spaced apart but the instrument contacts 17 are aligned with and can initially penetrate the openings 46 associated with the outer end plate 36, substantially as illustrated by FIG. 7. In this latter position as illustrated by FIG. 7, however, the battery is still isolated and hence not electrically coupled to the instrument. With slight additional insertion force applied to the battery pack 21, however, the battery pack 21 moves from the FIG. 7 position into the fully seated position illustrated by FIG. 8. This latter movement into the seated position of FIG. 8 causes the instrument contacts 17 to engage the bridging contacts 45, thereby causing the center part 42 of the membrane 34 to resiliently deflect and hence causes the contacts 45 to move inwardly toward and ultimately contactingly engage the live contacts 32, the latter being capable of at least limited resilient deflection so as to provide the desired intimate contact with the bridging contacts 45. When in the fully connected position illustrated by FIG. 8, the live battery contacts 32 hence engage the bridging contacts 45, the latter in turn engage the instrument contacts 17 to hence supply direct current from the battery pack to the internal electrical structure of the instrument, such as to the control board 16.

Figure 8:
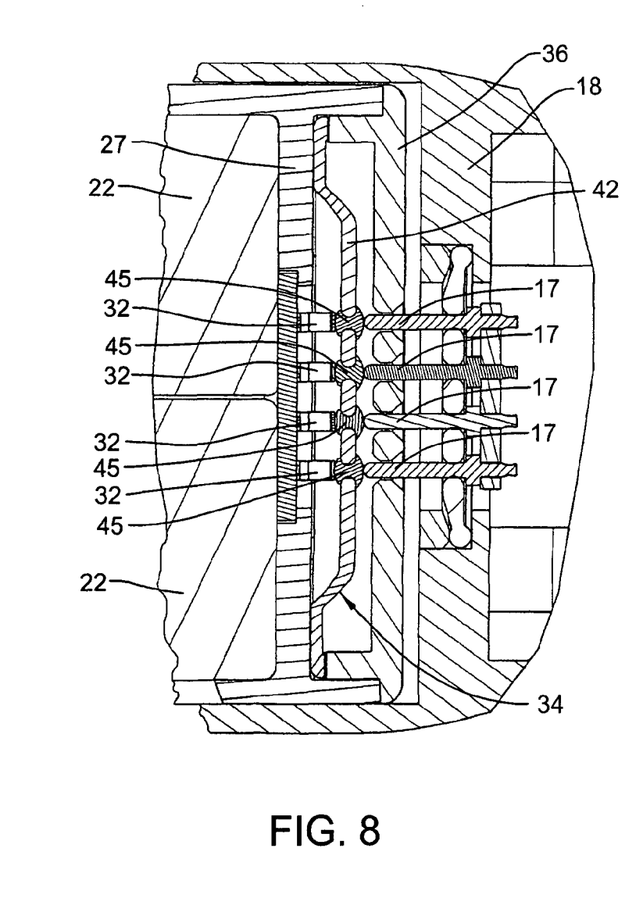
FIG. 8 is an enlarged fragmentary sectional view which generally corresponds to FIG. 7 but which illustrates the battery pack fully engaged within the instrument so that the battery contacts are engaged with the instrument contact to permit supply of electrical power to the instrument.

It will be appreciated that the instrument housing could be provided with a manual slide switch or similar cam which itself can be utilized for moving the battery pack 21 between the engaged position of FIG. 8 and the non-engaged position of FIG. 7 so as to permit decoupling of the battery from the instrument and hence permit the instrument to be maintained in a non-energized standby condition when desired.

Figure 9:
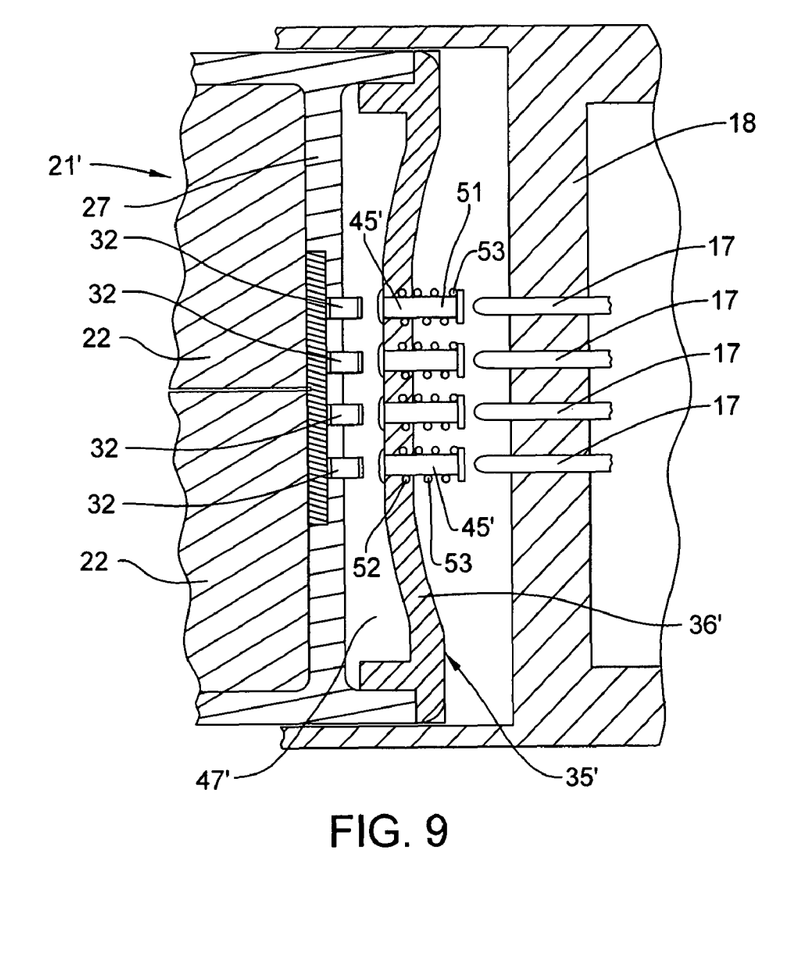
FIG. 9 is a view similar to FIG. 7 but illustrates a modified construction of the battery pack with respect to construction of the outer end wall of the battery pack enclosure and the manner of mounting the intermediate grouping of contacts thereon.

While the embodiment of the battery pack described above mounts the bridging contacts 45 on a resiliently deflectable member 34 which is supported and effectively carried on the end cap of the enclosure, it will be appreciated that the bridging contacts can be resiliently and movably supported using other structural arrangements, for example by individually resiliently supporting the bridging contacts directly on the outer end wall of the enclosure. Such a modified arrangement is illustrated in FIG. 9. This latter embodiment utilizes the same reference numerals utilized to designate corresponding parts of the embodiment of FIGS. 1-8, except for addition of a prime (') thereto so as to simplify additional description of this FIG. 9 embodiment.

In this FIG. 9 embodiment, the bridging contacts 45' which define the contact grouping associated with the end wall 36' are defined by individual members which are individually slidably but sealingly supported on and protrude through the end wall 36'. More specifically, each bridging contact 45' is defined by an elongate pin or cylinder body 51 which slidably protrudes through an opening formed in the end wall 36', being sealingly engaged within the end wall by an appropriate seal ring 52. The body 51 defining the bridging contact 45' has an enlarged head at the outer end, and a suitable resilient element such as a small coil spring 53 surrounds the body 51 and cooperates between the enlarged head of the body and the end wall 36', whereby each contact 45' is urged outwardly into a limit position substantially as illustrated, being normally maintained in this outwardly urged position due to a stop or an enlargement defined on the inner end of the respective contact.

With the arrangement illustrated by FIG. 9, when the battery pack is inserted into the instrument housing, the bridging contacts 45' which are normally urged outwardly so as to be disengaged from the live battery contacts 32 initially align with the instrument contacts 17. When the battery pack 21' is moved leftwardly in FIG. 9 into a fully seated position similar to the position illustrated in FIG. 8, the contacts 45' engage the ends of the contacts 17, whereby contacts 45' are depressed inwardly (leftwardly in FIG. 9) as the battery pack 21' moves rightwardly toward the housing wall 14. The bridging contacts 45' are hence moved inwardly relative to the wall 36' against the urging of the springs 53, whereupon these contacts 45' move inwardly a sufficient extent as to move into contacting engagement with the live contacts 32 in the same manner as described above relative to FIGS. 7-8.

With the arrangement of FIG. 9, however, when the battery pack is placed in a sterilizer and the outer faces of the bridging contacts 45' are exposed to a sterilizing fluid, the fluid acts against the urging of the springs 53 over only a small area, namely the cross-sectional area of the body 51, whereby a relatively high pressure sterilizing fluid may be utilized, and yet such fluid will normally be incapable of overcoming the outward urging of the springs 53 so as to cause undesired inward depression of the bridging contacts 45'.

Although particular preferred embodiments of the invention have been disclosed in detail for illustrative purposes, it will be recognized that variations or modifications of the disclosed apparatus, including the rearrangement of parts, lie within the scope of the present invention.

What is claimed is:

1. In a medical endoscope having a sterilizable housing, a grouping of individual first electrical contacts mounted on a wall of said housing and accessible from an exterior side of said wall, said first contacts being joined to electrical control circuitry disposed within said housing, and a detachable battery pack having a grouping of individual second electrical contacts which are in contacting engagement with said first contacts when the battery pack is operatively coupled to said housing for supplying direct electrical current to said electrical control circuitry, the improvement wherein said battery pack comprises:
   an enclosed sterilizable enclosure defining therein a sealed battery chamber;
   one or more replaceable batteries removably positioned within said sealed battery chamber;
   a grouping of individual third electrical contacts mounted on said enclosure within said sealed chamber adjacent one end thereof, said grouping of third contacts being maintained in electrical engagement with said batteries positioned-within said sealed chamber;
   said enclosure having an end wall arrangement which sealingly closes off said one end of said sealed battery chamber;
   said grouping of second contacts being movably mounted on said end wall arrangement for movement between a disengaged position wherein the second contacts are spaced outwardly away from and are maintained in a non-engaged relationship relative to said third contacts, and a bridging position wherein the second contacts are displaced inwardly into electrical contacting engagement with said third contacts;
   said end wall arrangement including resilient means cooperating with said second contacts for normally urging said second contacts into said non-engaged position; and
   said second contacts, during mounting of said battery pack on said housing, being initially engaged with said first contacts which then cause said second contacts to be displaced into said bridging position;
   whereby said sealed battery pack, when disengaged from said housing, can be placed in direct contact with a sterilizing fluid which is prevented from directly contacting said third contacts.

2. A medical endoscope according to claim 1, wherein the resilient means associated with said battery pack includes a resiliently flexible diaphragm which sealingly closes off said one end of said sealed battery chamber, said second contacts being stationarily mounted on said diaphragm and protruding therethrough for contacting engagement at opposite ends thereof with said first and third contacts when in said bridging position, and said diaphragm resiliently urging said second contacts toward and into said disengaged position when the battery pack is disengaged from the endoscope housing.

3. A medical endoscope according to claim 1, wherein the end wall arrangement of said battery pack includes a stationary end wall adjacent said one end of said sealed battery chamber, said second contacts penetrating through said end wall and being sealingly but movable mounted thereon for movement between said non-engaged and bridging positions, and said resilient means comprising springs which resiliently urge the second contacts into said non-engaged position.

4. A medical endoscope according to claim 1, wherein the contacts defining one of the groupings of first and second contacts are elongated and cantilevered to permit initial engagement between the first and second contacts prior to operative seating of the battery pack on said endoscope housing, whereby final relative movement of the battery pack into seated engagement with the endoscope housing causes the third contacts to relatively move into engagement with the second contacts.

5. A medical endoscope according to claim 1, wherein the enclosure of the battery pack includes an opening adjacent the other end of the sealed battery chamber for permitting access to the batteries therein, and the enclosure including a removable cover for sealingly closing off said opening.

6. A medical endoscope according to claim 1, wherein the third contacts are resiliently deflectable when contacted by said second contacts.

7. A sterilizable battery pack for mounting on a portable hand-held battery-powered medical instrument, such as an endoscope, comprising:
   an enclosed sterilizable enclosure defining therein a sealed chamber for removably accommodating one or more batteries;
   one or more replaceable batteries removably positioned within said sealed chamber;
   a grouping of individual first electrical contacts mounted on said enclosure within said sealed chamber adjacent one end thereof, said grouping of first contacts being maintained in electrical engagement with said batteries as positioned within said sealed chamber;
   said enclosure having an end wall arrangement which sealingly closes off said one end of said sealed chamber;
   a grouping of second electrical contacts movably mounted on said end wall arrangement for movement between a first position wherein the second contacts are spaced outwardly from and are maintained in a non-engaged relationship relative to said first contacts, and a second position wherein the second contacts are displaced inwardly into electrical contacting engagement with said third contacts;
   said end wall arrangement including resilient means cooperating with said second contacts for normally urging said second contacts into said first position; and
   said second contacts being displaceable into contacting engagement with said first contacts when said battery pack is mounted on a medical instrument and said second contacts are maintained in engagement with third contacts provided on the medical instrument;
   said sealed battery pack, when disengaged from said medical instrument, being positionable in direct contact with a sterilizing fluid which is prevented from directly contacting said third contacts while said second contacts are maintained in non-engaged relationship relative to said first contacts.

8. A battery pack according to claim 7, wherein the resilient means associated with said battery pack includes a resiliently flexible diaphragm which sealingly closes off said one end of said sealed battery chamber, said second contacts being stationarily mounted on said diaphragm and protruding therethrough for contacting engagement at opposite ends thereof with said first and third contacts when in said bridging position, and said diaphragm resiliently urging said second contacts toward and into said disengaged position when the battery pack is disengaged from the endoscope housing.

9. A battery pack according to claim 7, wherein the end wall arrangement of said battery pack includes a stationary end wall adjacent said one end of said sealed battery chamber, said second contacts penetrating through said end wall and being sealingly but movable mounted thereon for movement between said non-engaged and bridging positions, and said resilient means comprising springs which resiliently urge the second contacts into said non-engaged position.

10. A battery pack according to claim 7, wherein the first contacts are resiliently deflectable when contacted by said second contacts.

11. A battery pack according to claim 7, wherein the enclosure of the battery pack includes an opening adjacent the other end of the sealed battery chamber for permitting access to the batteries therein, and the enclosure including a removable cover for sealingly closing off said opening.

* * * * *

UNITED STATES PATENT AND TRADEMARK OFFICE
CERTIFICATE OF CORRECTION

PATENT NO. : 7,872,446 B2
APPLICATION NO. : 12/152082
DATED : January 18, 2011
INVENTOR(S) : Reid Cover et al.

It is certified that error appears in the above-identified patent and that said Letters Patent is hereby corrected as shown below:

On the Title page, please correct:
(73) Assignee "Kalamazoo, MN" to --Kalamazoo, MI--.

Column 8, line 13 please correct:
"positioned-within" to --positioned within--.

Signed and Sealed this
Fifth Day of April, 2011

David J. Kappos
*Director of the United States Patent and Trademark Office*